| United States Patent [19] | [11] Patent Number: 4,652,441 |
| Okada et al. | [45] Date of Patent: Mar. 24, 1987 |

[54] PROLONGED RELEASE MICROCAPSULE AND ITS PRODUCTION

[75] Inventors: Hiroaki Okada, Suita; Yasuaki Ogawa, Ibaraki; Takatsuka Yashiki, Takarazuka, all of Japan

[73] Assignee: Takeda Chemical Industries, Ltd., Osaka, Japan

[21] Appl. No.: 667,096

[22] Filed: Nov. 1, 1984

[30] Foreign Application Priority Data

Nov. 4, 1983 [JP]  Japan ................. 58-207760

[51] Int. Cl.$^4$ .................... A61K 9/52; B01J 13/02
[52] U.S. Cl. ............................. 424/19; 264/4.6; 424/85; 424/DIG. 15; 428/402.2; 514/2; 514/800; 514/822; 514/963
[58] Field of Search ............ 264/4.6; 428/402.2; 424/19, 35; 514/963

[56] References Cited

U.S. PATENT DOCUMENTS

| 3,523,906 | 8/1970 | Vrancken et al. ............ 264/4.6 |
| 3,691,090 | 9/1972 | Kitajima et al. ............. 264/4.6 X |
| 3,773,919 | 11/1973 | Boswell et al. ............... 424/19 |
| 4,234,571 | 11/1980 | Nestor et al. ................ 424/177 |
| 4,272,398 | 6/1981 | Jaffe ............................ 424/19 X |
| 4,273,920 | 6/1981 | Nevin ........................... 528/361 |

FOREIGN PATENT DOCUMENTS

| 52510 | 5/1982 | European Pat. Off. . |
| 58481 | 8/1982 | European Pat. Off. . |
| 13703 | 8/1967 | Japan . |

OTHER PUBLICATIONS

*The Pharmacopoeia of Japan*, 10th Edition, 1981, English version, Society of Japanese Pharmacopoeia, Yakuji Nippo, Ltd., 1982, pp. 16-21.
Microcapsule, Industrial Technology Library 25, pp. 102-103 (1971).
Journal of the Chemical Society of Japan vol. 72, pp. 493-499 (1969).

*Primary Examiner*—Richard D. Lovering
*Attorney, Agent, or Firm*—Wegner & Bretschneider

[57] ABSTRACT

A microcapsule produced by preparing a water-in-oil emulsion comprising an inner aqueous layer containing said water-soluble drug and a drug retaining substance therefor and an oil layer containing a polymer substance, then thickening or solidifying said inner aqueous layer to a viscosity of not lower than about 5000 centiposes and finally subjecting the resulting emulsion to in water drying gives prolonged release of water-soluble drug.

9 Claims, No Drawings

PROLONGED RELEASE MICROCAPSULE AND ITS PRODUCTION

This invention relates to a prolonged release microcapsule of water-soluble drug, and a method for producing the same.

A variety of dosage forms have been proposed for drugs which require long-term repeated administration. As one of such dosage forms, European patent application Publication No. 52,510 discloses a microcapsule prepared by the phase separation technique using a coacervating agent such as mineral oils and vegetable oils. However, microcapsules prepared by this and other analogous processes have the disadvantage that there tends to occur an inter-adhesion of particles in the course of production.

Under the circumstances, the present inventors conducted studies to develop a prolonged release preparation of water-soluble drug and found that a microcapsule having excellent properties can be produced with good efficiency by interposing a step of thickening of solidifying the inner aqueous layer of water in oil emulsion in the course of microencapsulation by in water drying process. The above finding was followed by further studies, which have resulted in the present invention.

The prolonged release microcapsule of the present invention is made by preparing a water-in-oil emulsion comprising an inner aqueous layer containing said water-soluble drug and a drug retaining substance therefor and an oil layer containing a polymer substance (microcapsule wall substance) then thickening or solidifying said inner aqueous layer to a viscosity of not lower than about 5000 centipoises and finally subjecting the resulting emulsion to in water drying process.

The water-soluble drug employed in the practice of this invention is a drug which is highly hydrophilic and has a low oil/water partition ratio. The term "low oil/water partition" ratio means that the octanol/water partition ratio, for instance, is not greater than about 0.1.

There is no particular limitation on the kind and type of said water-soluble drug. Thus, for example, biologically active polypeptides and other antibiotics, antitumor agents, antipyretics, analgesics, antiinflammatory agents, antitussives and expectorants, sedatives, muscle relaxants, antiepileptics, antiulcer agents, antidepressants, antiallergic drugs, cardiotonics, antiarrhythmic agents, vasodilators, antihypertensive diuretics, antidiabetics, anticoagulants, haemostatics, antituberculotics, hormone drugs, antinarcotics, etc. may be used as the water-soluble drug.

The biologically active polypeptides which are employed in accordance with this invention are preferably those consisting of two or more amino acid units and having a molecular weight between about 200 and about 80,000.

Examples of such polypeptides include luteinizing hormone releasing hormone (LH-RH) and its derivatives having LH-RH like activity, i.e. the polypeptides of the formula (I):

(Pyr)Glu-R$_1$-Trp-Ser-R$_2$-R$_3$-R$_4$-Arg-Pro-R$_5$     (I)

[wherein R$_1$ is His, Tyr, Trp or p-NH$_2$-Phe; R$_2$ is Tyr or Phe; R$_3$ is Gly or a D-amino acid residue; R$_4$ is Leu, Ile or Nle; R$_5$ is Gly-NH-R$_6$ (R$_6$ is H or a lower alkyl group which may optionally be substituted by OH) or NH-R$_6$ (R$_6$ is as defined above) or salts thereof] [see U.S. Pat. Nos. 3,853,837, 4,008,209 and 3,972,859, British Pat. No. 1,423,083, Proceedings of the National Academy of Sciences of the United States of America 78, 6509–6512 (1981)].

Referring to the above formula (I), the D-amino acid residue designated by R$_3$ may be an α-D-amino acid residue of up to 9 carbon atoms (e.g. D-Leu, Ile, Nle, Val, Nval, Abu, Phe, Phg, Ser, Thr, Met, Ala, Trp, α-Aibu), and these may have suitable protective groups (e.g. t-butyl, t-butoxy, t-butoxycarbonyl, naphthyl). Of course, acid salts and metal complex compounds of peptides (I) can also be used in the same manner as the aforementioned peptides (I).

In this specification, when amino acids, peptides, protective groups, etc. are mentioned, in connection with polypeptides (I), by abbreviations, such abbreviations are those established by IUPAC-IUB Commission on Biochemical Nomenclature or those used commonly in the particular field of art and when there may exist optical isomers of such amino acids, L-forms are intended unless otherwise indicated.

It should be understood that acetate of the polypeptide of formula (I) wherein R$_1$=His, R$_2$=Tyr, R$_3$=D-Leu, R$_4$=Leu, and R$_5$=NHCH$_2$-CH$_3$ is referred to as TAP-144 in experimental and working examples.

As examples of such polypeptides, LH-RH antagonists (U.S. Pat. Nos. 4,086,219, 4,124,577, 4,253,977, 4,317,815, 329,526, and 368,702) may be mentioned.

As further examples of said polypeptides may be mentioned insulin, somatostatin, somatostatin derivatives (U.S. Pat. Nos. 4,087,390, 4,093,574, 4,100,117 and 4,253,998), growth hormones, prolactin, adrenocorticotropic hormone (ACTH), melanocyte stimulating hormone (MSH), thyroid hormone releasing hormone (TRH), its salts, and derivatives thereof (U.S. Pat. Nos. 3,957,247 and 4,100,152), thyroid stimulating hormone (TSH), luteinizing hormone (LH), follicle stimulating hormone (FSH), vasopressin, vasopressin derivatives [desmopressin [Folia Endocrinologica Japonica 54, No. 5, p. 676–691 (1978)]], oxytocin, calcitonin, parathyroid hormone, glucagon, gastrin, secretin, pancreozymin, cholecystokinin, angiotensin, human placental lactogen, human cholionic gonadotropin (HCG), enkephalin, enkephalin derivatives [U.S. Pat. No. 4,277,394, European patent application Publication No. 31567], endorphin, kyotorphin, interferons (α, β, γ), interleukins (I, II, and III), taftsin, thymopoietin, thymosin, thymostimulin, thymic humoral factor (THF), serum thymic factor (FTS), and its derivatives (U.S. Pat. No. 4,229,438) and other thymic factors [Medicine in Progress 125, No. 10, p. 835–843 (1983)], tumor necrosis factor (TNF), colony stimulating factor (CSF), motilin, dinorphin, bombesin, neurotensin, cerulein, bradykinin, urokinase, asparaginase kallikrein, substance P analogue and antagonist, nerve growth factor, blood coagulation factors VIII and IX, lysozyme chloride, polymixin B, colistin, gramicidin, bacitracin, protein synthesis stimulating peptides (British patent No. 8232082), gastric inhibitory polypeptide (GIP), vasoactive intestinal polypeptide (VIP), platelet-derived growth factor (PDGF), growth hormone releasing factor (GRF, somatocrinin), bone morphogenetic protein (BMP), epidemale growth factor (EGF), etc.

As examples of said antitumor agents, may be mentioned bleomycin hydrochloride, methotrexate, actinomycin D, mitomycin C, vinblastine sulfate, vincristine sulfate, daunorubicin hydrochloride, adriamycin, neocarcinostatin, cytosine arabinoside, fluorouracil, tetrahydrofuryl-5-fluorouracil, krestin, picibanil, lentinan, levamisole, bestatin, azimexon, glycyrrhizin, poly I:C, poly A:U and poly ICLC.

As examples of said antibiotics, may be mentioned gentamicin, dibekacin, kanendomycin, lividomycin, tobramycin, amikacin, fradiomycin, sisomicin, tetracycline hydrochloride, oxytetracycline hydrochloride, rolitetracycline, doxycycline hydrochloride, ampicillin, piperacillin, ticarcillin, cephalothin, cephaloridine, cefotiam, cefsulodin, cefmenoxime, cefmetazole, cefazolin, cefotaxime, cefoperazone, ceftizoxime, moxolactam, latamoxef, thienamycin, sulfazecin, and azthreonam.

The aforementioned antipyretic, analgesic and antiinflammatory drugs include, for instance, sodium salicylate, sulpyrine, sodium flufenamate, sodium diclofenac, sodium indomethacin, morphine hydrochloride, pethidine hydrochloride, levorphanol tartrate and oxymorphone. As examples of said antitussives and expectorants may be mentioned ephedrine hydrochloride, methylephedrine hydrochloride, noscapine hydrochloride, codeine phosphate, dihydrocodeine phosphate, alloclamide hydrochloride, chlophedianol hydrochloride, picoperidamine hydrochloride, cloperastine, protokylol hydrochloride, isoproterenol hydrochloride, salbutamol sulfate and terbutaline sulfate. Examples of said sedatives include chlorpromazine hydrochloride, prochlorperazine, trifluoperazine, atropine sulfate and scopolamine methylbromide. The muscle relaxants include, among others, pridinol methanesulfonate, tubocurarine chloride and pancuronium bromide. The antiepileptics include, for instance, sodium phenytoin, ethosuximide, sodium acetazolamide and chlordiazepoxide hydrochloride. Examples of said antiulcer drugs include metoclopramide and L-histidine monohydrochloride. Examples of said antidepressants include imipramine, clomipramine, noxiptiline and phenelzine sulfate. The antiallergic drugs include, among others, diphenhydramine hydrochloride, chlorpheniramine maleate, tripelenamine hydrochloride, methdilazine hydrochloride, clemizole hydrochloride, diphenylpyraline hydrochloride and methoxyphenamine hydrochloride. The cardiotonics include, among others, trans-$\pi$-oxocamphor, theophyllol, aminophylline and etilefrine hydrochloride. The antiarrythmic agents include, for instance, propranolol hydrochloride, alprenolol hydrochloride, bufetolol hydrochloride and oxyprenolol hydrochloride. The vasodilators include, among others, oxyfedrine hydrochloride, diltiazem hydrochloride, tolazoline hydrochloride, hexobendine and bamethan sulfate. The antihypertensive diuretics include, among others, hexamethonium bromide, pentolinium, mecamylamine hydrochloride, ecarazine hydrochloride and clonidine hydrochloride. Examples of said antidiabetics include sodium glymidine, glypizide, phenformin hydrochloride, buformin hydrochloride and metformin. The anticoagulants include, among others, sodium heparin and sodium citrate. The haemostatic agents include, among others, thromboplastin, thrombin, menadione sodium bisulfite, acetomenaphthone, $\epsilon$-amino-caproic acid, tranexamic acid, carbazochrome sodium sulfonate and adrenochrome monoaminoguanidine methanesulfonate. Among said antituberculotics are isoniazid, ethambutol and sodium p-aminosalicylate. The hormone drugs are exemplified by prednisolone succinate, prednisolone sodium phosphate, dexamethasone sodium sulfate, betamethasone sodium phosphate, hexestrol phosphate, hexestrol acetate and methimazole. The antinarcotic agents include, among others, levallorphan tartrate, nalorphine hydrochloride and naloxone hydrochloride.

The proportion of said water-soluble drug depends on the kind of drug, expected pharmacological effect and its duration etc. but its concentration in the inner aqueous layer is selected from the range of about 0.001% to about 90% (w/w) and preferably 0.01% to 80% (w/w).

The drug retaining substance employed in accordance with this invention is either a substance which is soluble in water and hardly soluble in the organic solvent contained in said oil layer and when dissolved in water assumes a viscous semi-solid consistency or a substance which gains considerably in viscosity to provide a semi-solid or solid matrix under the influence of an external factor such as temperature, pH, metal ions (e.g. $Cu^{++}$, $Al^{+++}$, $Zn^{++}$, etc.), organic acids (e.g. tartaric acid, citric acid, tannic acid, etc.), a salt thereof (e.g. calcium citrate, etc.), chemical condensing agents (e.g. glutaraldehyde, acetoaldehyde), etc.

As examples of such drug retaining substance may be mentioned natural or synthetic mucilages and high molecular weight compounds.

Among such natural mucilages are gum acacia, Irish moss, gum karaya, gum tragacanth, gum guaiac, gum xanthane, locust bean gum, etc., while natural high molecular weight compounds include, among others, various proteins such as casein, gelatin, collagen, albumin (e.g. human serum albumin), globulin, fibrin, etc. and various carbohydrates such as cellulose, dextrin, pectin, starch, agar, mannan, etc. These substances may be used as they are or in chemically modified forms, e.g. esterified or etherified forms (e.g. methylcellulose, ethylcellulose, carboxymethylcellulose, gelatin succinate, etc.), hydrolyzed forms (e.g. sodium alginate, sodium pectinate, etc.) or salts thereof.

As examples of said synthetic high molecular weight compounds may be mentioned polyvinyl compounds (e.g. polyvinyl pyrrolidone, polyvinyl alcohol, polyvinyl methyl ether, polyvinyl ether, etc.), polycarboxylic acids (e.g. polyacrylic acid, polymethacrylic acid, Carbopol [Goodrich & Co., U. S. A.], etc.), polyethylene compounds (e.g. polyethylene glycol, etc.) and polysaccharides (e.g. polysucrose, polyglucose, polylactose, etc.) and salts thereof.

Also included are those compounds which undergo condensation or cross-linking under the influence of said external factors to give molecular weight compounds.

Among the aforementioned compounds, gelatin, albumin, pectin and agar are particularly desirable.

These compounds may be used alone or in combination and while the proportion of such compounds depends on the kind of compound, it is selected from the range of about 0.05% to 80% (w/w) in terms of concentration in the inner aqueous layer, preferably from the range of about 0.1% to 50% (w/w) on the same basis. It should, however, be understood that such compounds must be used in sufficient amounts to ensure that the initial viscosity of the inner aqueous layer in the water-in-oil emulsion described hereinafter will be not lower than about 5000 centipoises (cps), preferably not lower than about 10000 cps, or the inner aqueous layer may be increased in viscosity to not lower than about 5000 cps, preferably not lower than about 10000 cps, or be solidified by external factors.

The aforementioned polymer substance employed in the oil layer are polymers hardly soluble or insoluble in water and biocompatible. As examples of such polymer substance may be mentioned biodegradable aliphatic polymers (e.g. polylactic acid, polyglycolic acid, polycitric acid, polymalic acid, etc.), poly-α-cyanoacrylic acid esters, poly-β-hydroxybutyric acid, polyalkylene oxalate (e.g. polytrimethylene oxalate, polytetramethylene oxalate, etc.), poly(ortho-esters), poly(orthocarbonate), other polycarbonate (e.g. polythylene carbonate, polyethylene propylene carbonate, etc.), polyamino acids (e.g. poly-γ-benzyl-L-glutamic acid, poly-L-alanine, poly-γ-methyl-L-glutamic acid, etc.) and so on. As further examples of biocompatible polymer substance may be mentioned, polystyrene, polyacrylic acid, polymethacrylic acid, copolymer of acrylic acid and methacrylic acid, nylon, tetron, polyamino acid, silicone polymer, dextran stearate, ethylcellulose, acetylcellulose, nitrocellulose, polyurethane, maleic anhydride copolymers, ethylene-vinyl acetate copolymer, polyvinyl acetate, polyvinyl alcohol, polyacrylamide, etc. These polymer substances may be used alone or in the form of copolymers or mixtures of two or more species or of salts.

When used in injectable preparations, biodegradable polymers, among said polymers substances, are especially desirable, and as preferable examples of such polymer substance may be mentioned polylactic acid and a copolymer of lactic acid and glycolic acid and these mixtures.

The average molecular weight of such a polymer substance as used in accordance with this invention preferably ranges from about 2000 to about 800000 and is more desirably selected from the range of about 5000 to about 200000.

When a lactic acid-glycolic acid copolymer is used as said polymer, its comonomer ratio is preferably in the range of about 100/0 through about 50/50.

The proportion of such a polymer substance depends on the strength of pharmacological activity of the watersoluble drug used and the rate and duration of release of the drug. By way of illustration, the proportion of this polymer substance may range from 1/5 to 10000 times and preferably 1 to 1000 times the weight of the water-soluble drug.

The concentration of said polymer substance in the oil layer is about 0.5 to 90% (w/w) and preferably about 2 to 60% (w/w).

The solution containing said polymer substance (oil layer) is a solution of the polymer substance in a solvent. The solvent for this purpose should be one which boils at a temperature up to about 120° C. and is immiscible with water and capable of dissolving the polymer substance and as such there may be mentioned halogenated alkanes (e.g. dichloromethane, chloroform, chloroethane, dichloroethane, trichloroethane, carbon tetrachloride, etc.), ethyl acetate, ethyl ether, cyclohexane, benzene, n-hexane and toluene. These solvents may be used alone or in combination. nation.

With regard to the microencapsulation procedure, the drug retaining substance in an amount sufficient to give the aforementioned concentration is first dissolved in water and, then, the water-soluble drug is added in an amount sufficient to give the aforementioned concentration, whereby an inner aqueous layer is provided.

As a pH-adjusting agent for maintaining the stability and solubility of the water-soluble drug, there may be incorporated in this inner aqueous layer such an additive as carbonic acid, acetic acid, oxalic acid, citric acid, tartaric acid, succinic acid or phosphoric acid, sodium or potassium salts thereof, hydrochloric acid or sodium hydroxide. Moreover, as a stabilizer for the watersoluble drug, there may also be added such an agent as albumin, gelatin, citric acid, ethylenediamine sodium tetraacetate, dextrin, sodium hydrosulfite, etc. The inner aqueous layer may also contain a preservative such as p-oxybenzoic acid esters (e.g. methylparaben, propylparaben, etc.), benzyl alcohol, chlorobutanol, thimerosal, etc.

The inner aqueous layer thus prepared is poured into a solution of said polymer substance (oil layer) and the mixture is emulsified to give a water-in-oil emlusion.

The emulsification can be effected by the conventional dispersion techniques. For example, intermittent shaking, mixing by means of a propeller mixer, turbine mixer or the like, colloid mill operation, mechanical homogenization, ultrasonication, etc. may be utilized.

When the viscosity of the inner aqueous layer in such a water-in-oil emulsion is more than about 5000 centipoises or preferably over about 10000 centipoises from the beginning, the emulsion is immediately subjected to a desorption procedure but, otherwise, resort is had to an external factor to thicken the inner aqueous layer to a viscosity over about 5000 centipoises or preferably over about 10000 centipoises or solidify the same.

Exemplary procedures for increasing the viscosity include a heat treatment, cooling to a low temperature, freezing, rendering the pH acidic or alkaline, or adding such an agent as metal ions (e.g. iron ion for gum acacia, copper ion for carboxymethylcellulose, or calcium or magnesium ion for sodium pectinate) or organic acids or salts thereof (e.g. calcium citrate for sodium alginate, or adipic acid or tartaric acid for polyvinyl alcohol). There may also be mentioned the technique of cross-linking and condensing the polymer substance in the inner aqueous layer using a chemical condensing agent (e.g. glutaraldehyde, acetaldehyde, etc.).

With regard to the heat treatment, the procedure must be carried out in a closed vessel so as to avoid evaporation of the solvent contained in the oil layer. The temperature is virtually optional only if it is higher than the gelation temperature. Taking proteins as an example, the temperature is generally about 40° to 120° C. and the time is about 5 minutes to about 8 hours. This treatment thickens or solidifies the inner aqueous layer.

The technique of cooling the emulsion to a low temperature comprises cooling it to about -5° C. to about 35° C. and maintaining the low temperature with stirring for about 1 minute to 6 hours. In the case of agar whose gelation point is about 40° C., the emulsification is conducted under heating at about 50° to 80° C. and, then, caused to gel at the above-mentioned temperature. For all types of inner aqueous layer, it may be frozen by cooling at about -60° C. to 0° C. but the temperature should not be below the solidification point of the oil layer.

As regards the procedure of adding a metal ion, an organic acid or a salt thereof, the amount thereof depends on the amount of the drug retaining substance in the inner aqueous layer and may range from about ¼ to 20 molar equivalents and preferably from about 1 to 10 molar equivalents. The time required for said thickening or solidification is preferably not more than about 6 hours.

With regard to the technique of cross-linking and condensing the high molecular compound in the inner aqueous layer with chemical condensing agent, such condensing agent may for example be an aqueous solution of glutaraldehyde or acetaldehyde or a solution of the same in an organic solvent such as halogenated alkanes (e.g. chloroform, dichloromethane, etc.), toluene, etc. Particularly, a solution in the latter solvent which is miscible with the solvent used in the oil layer is desirable, because the particle size of the inner aqueous layer is not increased. The chemical condensing agent is added in a proportion of about 2 to 5 molar equivalents based on the drug retaining substance in the inner aqueous layer and the mixture is reacted under stirring for about 1 to 10 hours.

More specifically, taking gelatin as an example of said drug retaining substance, a water-in-oil emulsion of predetermined particle size is first prepared and then cooled to about 0° to 10° C. about 5 to 30 minutes with constant stirring, whereby the inner aqueous layer is caused to gel into semi-solid consistency. When agar is used as the drug retaining substance, the desired semi-solid consistency can be obtained by using a somewhat lower concentration than in the case of gelatin and the same procedure as that for gelatin. When albumin is employed, solidification is effected with a condensing agent such as glutaraldehyde. In this case, the water-soluble drug is dissolved in a ca. 5 to 50% aqueous solution of human serum albumin and the resulting solution is added to the organic solvent solution of high polymer to prepare a water-in-oil emulsion. Thereto is added a ca. 1 to 50% solution of glutaraldehyde in an organic solvent miscible with the oil layer and the mixture is reacted under stirring for about 1 to 10 hours so as to solidify the inner aqueous layer. In this procedure, albumin may be replaced with other substances that can be thickened or solidified by cross-linking and condensation, such as globulin, gelatin, casein, collagen and other polyamino acids. After the reaction, a compound which is ready to react with the condensing agent, e.g. an amino compound such as ethanolamine, aminoacetic acid, etc., may be added so as to inactivate the residual condensing agent.

When a substance capable of increasing in viscosity on alteration of pH, such as carboxyvinyl polymer (Carbopol, B. F. Goodrich, U.S.A.) is added to the inner aqueous layer, a ca. 1 to 20% solution of sodium hydroxide in ethanol or methanol is separately prepared and a small quantity of the solution is added to the water-in-oil emulsion to increase the viscosity of the inner aqueous layer.

The water-in-oil emulsion thus prepared is subjected to in water drying. Thus, this water-in-oil emulsion is added to a third aqueous layer to give a W/O/W ternary layer emulsion and, finally, the solvent in the oil layer is desorbed to give microcapsules.

An emulsifying agent may be added to the third or outer aqueous layer. It may be virtually any emulsifier that forms a stable oil-in-water emulsion, and is thus exemplified by anionic surfactants (e.g. sodium oleate, sodium stearate, sodium laurylsulfate, etc.), nonionic surfactants (e.g. polyoxyethylene sorbitan fatty acid esters [Tween 80 and Tween 60, Atlas Powder, U.S.A.], polyoxyethylene castor oil derivatives [HCO-60 and HCO-50, Nikko Chemicals, Japan], etc.), polyvinyl pyrrolidone, polyvinyl alcohol, carboxymethylcellulose, lecithin, gelatin, etc. Such emulsifiers may be used either alone or in combination. The concentration of the emulsifier may be selected from the range of about 0.01% to 20% and is preferably in the range of about 0.05% to 10%.

The aforesaid desorption of the solvent from the oil layer can be accomplished by the conventional technique. Thus, such desorption is effected by gradual decrease of pressure under agitation with a propeller mixer or magnetic stirrer or by adjusting the degree of vacuum in a rotary evaporator. The higher the stirring speed is, the smaller the diameter of the product microcapsule is. The time required for such procedures can be shortened by warming the W/O/W emulsion by degrees so as to make the solvent desorption thorough, after the solidification of the polymer has progressed to some extent and the loss of the drug from the inner aqueous layer has decreased. When the thickening or solidification is effected by techniques other than temperature control, the desorption may be effected by allowing the W/O/W emulsion to stand under stirring, warming the emulsion or blasting it with nitrogen gas. The process of desorption of the solvent is an important process having great bearing on the surface structure of microcapsules which governs the release of the drug. For example, when the desorption speed is increased, pits in the surface layer increase in number and size so that the release rate of the drug is increased.

The microcapsules obtained in the above manner are recovered by centrifugation or filtration, and the free water-soluble drug, emulsifying agents, etc. on the surface are removed by repeated washing with water, then, if necessary, the microcapsules are warmed under reduced pressure to achieve a complete removal of moisture and of the solvent from the microcapsule wall.

The above microcapsules are gently crushed and sieved, if necessary, to remove coarse microcapsules. The particle size of microcapsules depends on the desired degree of prolonged release. When they are to be used as a suspension, its size may be within the range satisfying the required dispersibility and needle pass requirements. For example, the average diameter may range from about 0.5 to 400 $\mu$m and preferably from about 2 to 200 $\mu$m.

The method of this invention enables one to apply a high shear stress in the preparation of the W/O/W emulsion with less breakdown of the inner aqueous layer and facilitates particle size control to thereby provide fine microcapsules with good efficiency. The additional commercial advantage of this invention is that the required quantity of organic solvent is as small when compared with the drying-in-oil technique.

Moreover, the microcapsules produced by the method of this invention feature a reduced coalescence of individual microcapsules during production so that they are more truly spherical in configuration. In addition, desorption of the solvent from the oil layer can be easily controlled to adjust the surface structure (for example, the number and size of fine holes which serve as main routes of the drug release) of microcapsules.

The microcapsules according to this invention can be administered in clinical practice directly as fine granulets or as formulated preparation into a variety of preparations. Thus, they can be used as raw materials for the production of final pharmaceutical preparations.

Such preparations include, among others, injections, oral preparations (e.g. powders, granules, capsules, tablets, etc.), nasal preparations, suppositories (e.g. rectal, vaginal), and so on.

If the microcapsules according to this invention are to be processed into an injectable preparation, they are dispersed in an aqueous vehicle together with a dispersing agent (e.g. Tween 80, HCO-60 (Nikko Chemicals), carboxymethylcellulose, sodium alginate, etc.), preservative (e.g. methyl-paraben, propyl-paraben, benzyl alcohol, chlorobutanol, etc.), isotonizing agent (e.g. sodium chloride, glycerin, sorbitol, glucose, etc.), etc. The vehicle may also be a vegetable oil (e.g. olive oil, sesame oil, peanut oil, cottonseed oil, corn oil, etc.), propylene glycol or the like. In this manner, a prolonged release injection can be produced.

The prolonged release injection made from said microcapsules may be further supplemented with an excipient (e.g. mannitol, sorbitol, lactose, glucose, etc.), redispersed, and then be solidified by freeze-drying or spray-drying, and on extemporaneous addition of a distilled water for injection or suitable vehicle for the reconstitution, such preparation gives a prolonged release injection with greater stability.

If the microcapsules according to this invention are to be processed into tablets, they are mixed with an excipient (e.g. lactose, sucrose, starch, etc.), disintegrating agent (e.g. starch, calcium carbonate, etc.), binder (e.g. starch, gum arabic, carboxymethylcellulose, polyvinylpyrrolidone, hydroxypropylcellulose, etc.) or/and lubricant (e.g. talc, magnesium stearate, polyethylene glycol 6000, etc.), and the mixtures are compressed in molds.

To manufacture a nasal preparation from the microcapsules according to this invention, they are provided solid, semi-solid or liquid state in the conventional manner. To manufacture the solid nasal preparation for instance, the microcapsules either as they are or together with an excipient (e.g. glucose, mannitol, starch, microcrystalline cellulose, etc.) and/or thickener (e.g. natural mucilages, cellulose derivatives, polyacrylates, etc.) are processed into a powdery composition. To make a liquid composition, the microcapsules are processed into an oily or aqueous suspension in substantially the same manner as in the case of injections. The semi-solid preparation may be an aqueous or oily gel or ointment. In any case, there may be added a pH adjusting agent (e.g. carbonic acid, phosphoric acid, citric acid, hydrochloric acid, sodium hydroxide, etc.), a preservative (e.g. p-hydroxybenzoic acid esters, chlorobutanol, benzalkonium chloride, etc.), etc.

A suppository of the microcapsules according to this invention, whether in oily or aqueous solid or semi-solid state or in liquid state, can be produced in the per se conventional manner. The kind of oleagenous base for such composition is optional only if it will not dissolve the microcapsules. Thus, for example, higher fatty acid glycerides [e.g. cacao butter, Witepsol (Dynamit-Novel, West Germany), etc.], intermediate fatty acids [e.g. Miglyol (Dynamit-Novel), etc.]and vegetable oils (e.g. sesame oil, soybean oil, cottonseed oil, etc.) may be mentioned. The aqueous base is exemplified by polyethylene glycol and propylene glycol, while the aqueous gel base may be selected from among natural mucilages, cellulose derivatives, vinyl polymers, polyacrylates, etc.

The dosage of the prolonged release preparation according to this invention depends on the kind and amount of the active ingredient (i.e. water-soluble drug), dosage form, duration of drug release, recipient animal (e.g. warm-blooded animals such as mouse, rat, horse, cattle, man), and object of treatment. It is, however, sufficient to ensure that the effective dose of the active ingredient will be administered. For example, the amount per dose to humans may be selected from the range of about 1 mg to 10 g, preferably about 10 mg to 2 g, in terms of the weight of microcapsules.

When an injectable dosage form is employed, the volume of the suspension may be selected from the range of about 0.1 to 5 ml, preferably about 0.5 to 3 ml.

In this manner, there are provided pharmaceutical compositions made up of a water-soluble drug, a drug retaining substance and a biocompatible polymer which are capable of continuous and prolonged release of the drug.

The prolonged release preparation according to this invention has the following and other advantages.

(1) The prolonged release of water-soluble drugs in various dosage forms can be ensured. Particularly when a long-term treatment with injections is required for the desired effect, the preparation helps achieve the desired pharmacological effects with an administration schedule of once a month or a week or even once a year, instead of giving injections every day. Moreover, compared with the conventional sustained release drugs, the prolonged release preparation according to this invention ensures longer sustained effects.

(2) When injections are prepared using biodegradable polymers, surgical procedures such as implantation are not required but the preparations can be administered subcutaneously or intramuscularly as easily as ordinary injectable suspensions, not entailing the need for removal from the body.

The preparation according to this invention can be directly administered to the tumor itself, the site of inflammation or the receptor region, so that systemic side effects can be controlled and the drug be allowed to act on the target organ for a longer time period with efficiency, thus making for increased drug efficacy. Moreover, it can be used in intra-arterial administration in the vascular embolic therapy proposed by Kato et al for cancer of the kidney and of the lung (Lancet II, 479–480, 1979).

(3) The release of the active ingredient is continuous, and in the case of antihormones, receptor antagonists, etc., greater pharmacological effects are obtained than by daily pulsatile administration.

(4) Since a drug retaining substance is employed, the water-soluble drug can be incorporated in the microcapsule more easily and efficiently than by the conventional drying-in-solvent technique. Moreover, the microcapsules are fine and more truly spherical in configuration.

(5) By varying the rate of desorption of the solvent from the polymer constituting the microcapsule wall, the number and size of fine holes in the surface layer of each microcapsule which are determinant of the rate of drug release can be freely controlled.

The following experimental and working examples are further illustrative of this invention.

EXPERIMENTAL EXAMPLE 1

The repeated administration of TAP-144 to mature female rats in massive doses causes desensitization of the pituitary-gonad system to thereby halt the sexual cycle in the diestrous stage. It is known that this halt of the sexual cycle is promptly recovered as the administration of TAP-144 is discontinued. Therefore, using this halt of the sexual cycle of female rats as an indicator, the present inventors investigated the durations of action of 7 different microcapsules prepared using different polymers, which are among the 8 kinds of microcapsules according to Example 1 and of two other microcapsules (No. 039 and No. 0310) which are produced by using TAP-144 for the inner aqueous layer in the amounts of ½ and 2.5 times, respectively, but in otherwise the same manner as Example 1. Thus, using SD female rats (aged 14 to 16 weeks) which are confirmed to show a normal 4-day cycle by the examination of vaginal smears during the preceding period of at least 1 week in groups of 5 individuals, each of the above-mentioned microcapsules is injected subcutaneously at the back of the neck in a dose of 3 mg/kg as TAP-144. Thereafter, the examination of vaginal smears is carried out every day to monitor changes in sexual cycle. The microcapsules are administered either in the form of oily suspensions in purified sesame oil or in the form of aqueous suspensions prepared using a dispersed vehicle constituted with 0.2% Tween 80, 0.5% sodium carboxymethylcellulose, 0.14% methyl-paraben, 0.014% propyl-paraben and 8% D-sorbitol in distilled water for injection.

The results are presented in Table 1. It will be apparent from Table 1 that all of the microcapsules according to this invention have every satisfactory durations of action.

TABLE 1

| Microcapsule No. | Formulation | Duration of action[a] (days) |
|---|---|---|
| 031 | Aqueous | ≧105 |
| 033 | Aqueous | 19.0 ± 0.6 |
| 033 | Oily | 19.2 ± 0.5 |
| 034 | Aqueous | ≧123 |
| 035 | Aqueous | 59.0 ± 7.6 |
| 036 | Aqueous | 117.2 ± 1.8 |
| 037 | Aqueous | 39.8 ± 1.8 |
| 038 | Aqueous | 35.0 ± 1.3 |
| 039 | Aqueous | 60.0 ± 6.2 |
| 0310 | Aqueous | 19.6 ± 0.4 |

[a]Mean ± standard error for 5 rats.

EXPERIMENTAL EXAMPLE 2

The repeated adminsitration of TAP-144 to male rats in massive doses causes an atropy (decrease of organ weight) of the inner genital organs due to desensitization of the pituitary-gonad system. Using this action, the duration of action of the TAP-144 microcapsules produced in Example 1 are investigated. Thus, No. 032 and No. 035 microcapsules according to Example 1 are injected subcutaneously at the back of the neck of SD male rats (aged 6 weeks) in the dose of 900 μg as TAP-144 after 1, 2 and 4 weeks the inner genital organs are removed and weighed. As control, untreated rats of the same age are used and the percentages of organ weights relative to the control organ weights are calculated. The results are shown in Table 2. In the group of rats given No. 032 microcapsules, no marked difference is found between oily and aqueous formulations and a marked weight decrease persisting for 4 weeks is noted in the weight of testis. A marked weight decrease is also observed in the seminal vesicle, with a significant difference being noted even at 2 weeks. In the No. 035 microcapsule group, too, marked weight decreases of both the testis and seminal visicle are found after 1 week. The above results indicate that the TAP-144 prolonged release injections according to this invention have satisfactory durations of action.

TABLE 2

| | | Microcapsule No. 032 | | Microcapsule No. 035 |
|---|---|---|---|---|
| Time | Organ | Oily | Aqueous | Aqueous |
| 1 Week | Testis | 58.1 ± 8.3** | 57.9 ± 7.4** | 62.4 ± 5.3**[a] |
| | Prostate | 94.6 ± 4.7 | 92.9 ± 9.9 | 86.7 ± 7.9 |
| | Seminal vesicle | 67.6 ± 10.6 | 62.7 ± 10.7* | 66.4 ± 7.7* |
| 2 Weeks | Testis | 53.4 ± 6.5** | 65.1 ± 10.6* | |
| | Prostate | 67.2 ± 6.3** | 85.1 ± 7.3 | |
| | Seminal vesicle | 39.5 ± 6.3** | 56.2 ± 7.8* | |
| 3 Weeks | Testis | 77.1 ± 5.7** | 58.0 ± 5.7** | |
| | Prostate | 97.4 ± 4.6 | 87.2 ± 5.9 | |
| | Seminal vesicle | 89.3 ± 2.7 | 80.5 ± 6.4* | |

[a]Percentages relative to the organ weights of control rats (untreated, the same age)
**A highly significant difference (P < 0.01) from control by t-test.
*A significant difference (P < 0.05) from control by t-test.

EXAMPLE 1

In 2.5 ml of a 20% aqueous gelatin solution prepared by warming (at 60° to 70° C.) is dissolved 200 mg of TAP-144 and the whole solution is added to 10 ml of a 20% dichloromethane solution of one of the 7 different lactic acid or lactic acid-glycolic acid polymers (2 runs for polylactic acid with a molecular weight of 50,000). The mixture is ultrasonicated (20 KHz, 100 W, a few minutes, the ultrasonicator manufactured by Ohtake Seisakusho Inc., Japan) to give a microfine W/O emulsion. This emulsion is immediately cooled with ice to cause gelation of the gelatin layer. This is then added to 100 ml of 0.5% polyvinyl alcohol (Gosenol EG-40, the Nippon Synthetic Chemical Industry Co., Ltd., Japan)-1/30 M phosphate buffer (pH 6.0) and dispersed using a homogenizer (T. K. Homomixer, Tokushu Kika Kogyo Inc., Japan, 30 V) (3,000 r.p.m.) for 15 seconds to give a W/O/W emulsion. This emulsion is quickly transferred to a rotary evaporator in which the dichloromethoane is desorbed under ice-cooling. After foaming has subsided, the emulsion is warmed to 30° to 40° C. in a constant-temperature water bath for complete desorption of the organic solvent. The hardened microcapsules are then filtered through a glass filter and washed 5 times with 10 ml portions of distilled water. They are then spread on a glass dish and allowed to dry under reduced pressure for 1 to 3 days. The product is sieved through a 100-mesh screen (Sieve opening: 147 μm) to give TAP-144 microcapsules.

In 10 ml of dichloromethane is dissolved 10 mg of the above microcapsules and TAP-144 in the solution is extracted with 10 ml of distilled water under shaking for 10 minutes. The TAP-144 content of the aqueous layer is assayed by high performance liquid chromatography (HPLC) and the percentage of TAP-144 taken up into the microcapsules relative to the initial amount of TAP-144 added is calculated. The results are shown in Table 3.

TABLE 3

| | Polymer | | |
|---|---|---|---|
| Microcapsule No. | Lactic acid/ glycolic acid | Mol. weight | Takeup (%) |
| Control | | | |
| 021 | 100/0 | 50000 | 6.7 |
| 022 | 100/0 | 50000 | 5.5 |
| 023 | 100/0 | 50000 | 1.9 |
| This invention | | | |
| 031 | 100/0 | 73000 | 70.4 |

TABLE 3-continued

| Microcapsule No. | Polymer Lactic acid/ glycolic acid | Mol. weight | Takeup (%) |
| --- | --- | --- | --- |
| 032 | 100/0 | 50000 | 70.7 |
| 033 | 100/0 | 50000 | 71.5 |
| 034 | 100/0 | 15000 | 54.8 |
| 035 | 100/0 | 6800 | 55.8 |
| 036 | 88.7/11.3 | 19000 | 44.0 |
| 037 | 78.1/21.9 | 10000 | 58.3 |
| 038 | 54.5/45.4 | 20000 | 53.1 |

It will be apparent from Table 3 that when the in water drying technique under the same conditions is carried out without gelation of the first aqueous layer (control), the takeup ratios are as low as 1.9 to 6.7% whereas the takeup ratios for the microcapsules according to this invention are as high as 44.0 to 71.5%. In the repeated experiments by the same production procedure using polylactic acid with a molecular weight of 50000, the take up ratio are almost comparable.

EXAMPLE 2

In a 20% aqueous gelatin solution prepared by warming (60° to 70° C.) is dissolved 200 mg of TAP-144. This solution is added when hot to a 20% dichloromethane solution of polylactic acid (average mol. wt. 50000) and the mixture is ultrasonicated in the same manner as Example 1 to give a fine W/O emulsion. Separately, 5 ml of a 25% aqueous solution of glutaraldehyde is extracted with 5 ml of dichloromethane (using the aforementioned ultrasonicator, 50 W, 2 min.) and the organic layer is added to the emulsion prepared above. Using a four-blade rotary mixer, the mixture is reacted at room temperature under agitation for 6 hours. Thereafter, 4 ml of ethanolamine is added and the reaction is further conducted for 1 hour. After ice-cooling, the reaction mixture is poured in 100 ml of ice-cooled 0.5% polyvinyl alcohol-1/30 M phosphate buffer (pH 6.0).

Then, as in Example 1, a W/O/W emulsion is prepared and the organic solvent is desorbed to give TAP-144 microcapsules (Microcapsule No. 0311). In addition, a 30% aqueous solution of human serum albumin in lieu of said 20% gelatin is treated with glutaraldehyde in the same manner as above to prepare TAP-144 microcapsules (Microcapsule No. 0312).

These microcapsules are dispersed in purified sesame oil and the dispersions are subcutaneously injected into mature female rats at a dose of 12 mg/kg as TAP-144 in the same manner as Experimental Example 1 to assess the durations of action of the respective prolonged release preparations.

The results are presented in Table 4. It will be seen that their actions last for about 4 months, indicating that these microcapsules are satisfactory prolonged release preparations.

TABLE 4

| Microcapsule No. | Drug retaining substance | Duration of action[a] (days) |
| --- | --- | --- |
| 0311 | 20% gelatin | ≧147 |
| 0312 | 30% human serum albumin | 114.8 ± 5.9 |

[a]Mean ± standard error for 5 rats

EXAMPLE 3

In 10 ml of dichloromethane is dissolved 3 g of lactic acid-glycolic acid copolymer (monomer ratio: 88.7/11.3, average mol. wt. 19000) followed by addition of 3 ml of a 30% aqueous solution of gelatin (dissolved at 60° C.) Then, a solution of 200 mg of LH-RH antagonist (N-Ac-[D-P-Cl-Phe$^{1,2}$, D-Trp$^3$,D-Arg$^6$, D-Ala$^{10}$]-LH-RH) (European patent application Publication No. 81,877) is added and the mixture is ultrasonicated in the same manner as Example 1 to give a W/O emulsion. This emulsion is immediately cooled with ice and dispersed in a water-cooled 0.5% aqueous solution of polyvinyl alcohol. Then, the dichloromethane is desorbed and LH-RH antagonist microcapsules recovered in the same manner as Example 1.

EXAMPLE 4

In 2.5 ml of a 20% aqueous solution of gelatin (prepared at 60° C.) is dissolved 500 mg of an enkephalin derivative (H-Tyr-D-Met(O)-Gly-EtPhe-NH-NHCOCH$_3$.AcOH) (U.S. Pat. No. 4,277,394, TAI-1399) and the solution is added to 10 ml of a 20% solution of polyactic acid (average mol. wt. 50000) in dichloromethane. The mixture is further worked up in the same manner as Example 1 to give a W/O emulsion. Under ice-cooling, this emulsion is further worked up in 0.5% polyvinyl alcohol-1/30 M phosphate buffer (pH 6.0) to give a W/O/W emulsion. The organic solvent is then desorbed under reduced pressure in a rotary evaporator and the mixture is warmed from ice-cooling to 35° C. and when foaming has subsided, it is sieved through a 100-mesh screen and filtered through a glass filter to give TAI-1399 microcapsules.

The microcapsules thus produced are washed 4 times with 10 ml portions of distilled water and redispersed in a mixed aqueous solution of 0.2% Tween 80, 0.5% sodium carboxymethylcellulose and 10% mannitol, followed by freezedrying to give a prolonged release preparation of TAI-1399 which is of a reconstituted suspension type and the action of which lasts in vivo for more than about 2 weeks.

EXAMPLE 5

In a 20% aqueous solution of gelatin (prepared at 60° C.) is dissolved 2.2 billion units of γ-interferon and the solution is added to 10 ml of a 20% dichloromethane solution of polylactic acid (average mol. wt. 73000). Then, the same procedure as Example 1 is followed to give a W/O/W emulsion under ice-cooling, remove the solvent in a rotary evaporator and recover solid microcapsules by filtration to give γ-interferon microcapsules.

The above microcapsules are washed 4 times with 10 ml portions of distilled water and dispersed in 50 ml of a mixed aqueous solution of 0.2% Tween 80, 0.5% sodium carboxymethylcellulose and 8% D-sorbitol, and 1 ml portions of the dispersion are distributed into glass vials and freeze-dried. The contents of each vial are extemporaneously redispersed in 1 ml of distilled water for injection containing 0.4% methyl-paraben and 0.04% propylparaben to give a prolonged release injection containing about 25,000 thousand units of γ-interferone per dose.

EXAMPLE 6

In 2.5 ml of distilled water are dissolved 300 mg of synthetic serum thymic factor (FTS: H-Glu-Ala-Lys-Ser-Gln-Ala-Gly-Ser-Asn-OH and 750 mg of human serum albumin, and the whole solution is added to 10 ml of a dichloromethane solution containing 3 g of lactic acid-glycolic acid copolymer (monomer ratio:

78.1/21.9, average mol. wt. 10000) Thereafter, the same procedure as Example 1 is followed to prepare a W/O emulsion. To this emulsion is added 3 ml of a dichloromethane extract of 25% aqueous glutaraldehyde (3 ml) and the reaction is carried out under stirring for 5 hours. Then, 3 ml of ethanolamine is added and the mixture is further stirred for 1 hour. This W/O/W emulsion is poured in 100 ml of a 0.5% aqueous solution of polyvinyl alcohol and the solution is worked up in the same manner as Example 1 to give a W/O/W emulsion. Finally, the solvent is removed in a rotary evaporator and the product microcapsules are recovered.

The microcapsules thus obtained are dispered in 20 ml of the same dispersing medium as the one used in Example 5 and 2 ml portions of the dispersion are distributed into glass vials and freeze-dried to give a prolonged release injection containing about 15 mg of FTS per dose.

EXAMPLE 7

In 2.5 ml of a 2% aqueous solution of agar (liquefied by warming at 60° C.) is dissolved citrate of a thyroid hormone derivative (DN-1417) of the following formula:

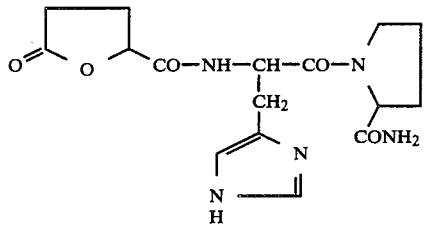

This solution is added to 10 ml of a 20% solution of polylactic acid (average mol. wt. 50000) in dichloromethane. The mixture is worked up in the same manner as Example 1 to give a W/O/W emulsion which is further processed into a W/O/W emulsion under ice cooling. Finally, the organic solvent is removed to give DN-1417 microcapsules.

These microcapsules are recovered by filtration, dried in vacuo at 40° C. for 24 hours and sieved through a 100-mesh screen. The product (500 mg) is filled into a vial to give a prolonged release injection containing about 75 mg of DN-1417 which is used by a reconstituted suspension.

EXAMPLE 8

In 10 ml of dichloromethane is dissolved 2 g of lactic acid-glycolic acid copolymer (monomer ratio: 54.5/45.5, average mol. wt. 20000). To this solution is added 3 ml of a 20% aqueous gelatin solution containing 400 mg of mitomycin C (liquified by warming at about 60° C.) and the mixture is worked up in the same manner as Example 1 to give mitomycin C microcapsules.

The microcapsules are dried in vacuo and sieved through a 100-mesh screen. A 200 mg of the product is taken as a prolonged release injection containing about 20 mg of mitomycin C which is a reconstituted suspension for injection.

EXAMPLE 9

To a 20% dichloromethane solution of lactic acid/glycolic acid copolymer (monomer ratio: 78.1/21.9, average mol. wt. 10000) is added 3 ml of a 20% aqueous gelatin solution containing 1.5 g of gentamycin sulfate (liquefied by warming). The mixture is further worked up in the same manner as Example 1 to give microcapsules.

These microcapsules are dried in vacuo and sieved, and 350 mg of the product is taken as a prolonged release preparation containing about 100 mg of gentamycin for use by a reconstituted suspension.

EXAMPLE 10

In 10 ml of dichloromethane is dissolved 3 g of polylactic acid (average mol. wt. 15000) followed by addition of 3 ml of a 20% aqueous gelatin solution containing 43000 units of blood coagulation factor VIII and 15 mg of sodium citrate. The mixture is worked up in the same manner as Example 4 to give microcapsules.

This product is dispersed in 20 ml of dispersing medium and 2 ml portions are filled into vials to freeze dry to give a prolonged release injection for a reconstituted suspension containing about 3000 units of blood coagulation factor VIII in each vial.

EXAMPLE 11

In 3 ml of a 20% aqueous gelatin solution (liquified by warming) is dissolved 2 g of sulpyrine and the solution is added to 10 ml of a 25% dichloromethane solution of lactic acid-glycolic acid copolymer (54.5/45.5, average mol. wt. 20,000). Finally, the mixture is worked up in the same manner as Example 1 to give microcapsules.

EXAMPLE 12

In 2.5 ml of 20% gelatin solution (liquified by warming) is dissolved 500 mg of morphine hydrochloride and the solution is added to 10 ml of a 20% dichloromethane solution of polylactic acid (average mol. wt. 15000). Thereafter, the same procedure as Example 1 is followed to give prolonged release microcapsules for injection.

EXAMPLE 13

In 2.5 ml of 20% aqueous gelatin solution (liquified by warming) is dissolved 150 mg of sodium diclofenac and the solution is added to 10 ml of a 20% dichloromethane solution of polylactic acid (average mol. wt. 15,000). The mixture is worked up in the same manner as Example 1 to give microcapsules for injection.

EXAMPLE 14

In 2.5 ml of a 20% aqueous gelatin solution (liquified by warming) is dissolved 1 g of methylephedrine hydrochloride and the solution is added to 10 ml of a 20% dichloromethane solution of polylactic acid (average mol. wt. 50,000). The mixture is worked up in the same manner as Example 1 to give methylephedrine microcapsules for injection

EXAMPLE 15

In 3.0 ml of 20% aqueous gelatin solution (liquified by warming) is dissolved 1 g of chlorpromazine hydrochloride, and the solution is added to 10 ml of a 20% dichloromethane solution of lactic acid-glycolic acid copolymer (88.7/11.3, average mol. wt. 19,000). The mixture is worked up in the same manner as Example 1 to give chlorpromazine hydrochloride microcapsules for injection.

EXAMPLE 16

In 3.0 ml of 30% gelatin (dissolved by warming) is dissolved 50 mg of pridinol methanesulfonate and the solution is added to 10 ml of a 30% dichloromethane solution of lactic acid-glycolic acid copolymer (78.1/21.9, average mol. wt. 10,000). The mixture is then worked up in the same manner as Example 1 to give pridinol methanesulfonate microcapsules for injection.

EXAMPLE 17

Using 600 mg of chlordiazepoxide hydrochloride, the procedure of Example 11 is followed to give microcapsules.

EXAMPLE 18

Using 800 mg of metoclopramide, the procedure of Example 12 is followed to give metoclopramide microcapsules for injection.

EXAMPLE 19

Using 1 g of imipramine, the procedure of Example 15 is followed to give imipramine microcapsules for injection.

EXAMPLE 20

Using 750 mg of diphenhydramine hydrochloride, the procedure of Example 14 is followed to give diphenhydramine hydrochloride microcapsules for injection.

EXAMPLE 21

Using 750 mg of etilefrin hydrochloride, the procedure of Example 15 is followed to give etilefrin hydrochloride microcapsules for injection.

EXAMPLE 22

Using 300 mg of propranolol hydrochloride, the procedure of Example 14 is followed to give propranolol hydrochloride microcapsules for injection.

EXAMPLE 23

Using 250 mg of oxyfedrine hydrochloride, the procedure of Example 12 is followed to give oxyfedrine hydrochloride microcapsules for injection.

EXAMPLE 24

Using 300 mg of pentolinium, the procedure of Example 11 is followed to give pentolonium microcapsules.

EXAMPLE 25

Using 1 g of phenformin hydrochloride, the procedure of Example 13 is followed to give phenformin hydrochloride microcapsules.

EXAMPLE 26

Using $2 \times 10^6$ units of sodium heparin, the procedure of Example 15 is followed to give sodium heparin microcapsules.

EXAMPLE 27

Using 400 mg of adrenochrome monoaminoguanidine methanesulfonate, the procedure of Example 12 is followed to give adrenochrome monoaminoguanidine methanesulfonate microcapsules for injection.

EXAMPLE 28

Using 800 mg of isoniazid, the procedure of Example 16 is followed to give isoniazid microcapsules for injection.

EXAMPLE 29

Using 750 mg of prednisolone sodium phosphate, the procedure of Example 15 is followed to give prednisolone sodium phosphate microcapsules for injection.

EXAMPLE 30

Using 100 mg of levallorphan tartrate, the procedure of Example 16 is followed to give levallorphan tartrate microcapsules for injection.

EXAMPLE 31

To 160 g (1.5 mol) of 85% lactic acid aqueous solution is added 38 g (0.5 mol) of glycolic acid, and the mixture is subjected to heating under reduced pressure in nitrogen gas stream at 100° to 150° C./350 to 30 mmHg stepwise for 6 hours with removing distilled water, and then the resultant is subjected to condensation reaction at 175° C./6 to 5 mmHg for 36 hours to give lactic acid-glycolic acid copolymer (monomer ratio: 75/25, average molecular weight 14,000).

In 10 ml of dichloromethane and 3 ml of n-pentane is dissolved 2 g of said lactic acid-glycolic acid copolymer which is synthesized without catalyst.

To this solution is added 2.5 ml of 20% aqueous gelatin solution containing 200 mg of TAP-144 which has been previously liquified by warming at about 60° C., and the mixture is ultrasonicated (100W, a few minutes), the given microfine W/O emulsion is immediately cooled down at about 15° C. to cause gelation of the gelatin. This is then added to 1000 ml of 0.5% polyvinyl alcohol in distilled water solution and dispersed using a homogenizer having a punching metal of 80 μm pores for 60 seconds at 3000 r.p.m. to give a W/O/W emulsion. The emulsion is quickly transferred to a vessel in which the dichloromethane and n-pentane are desorbed under mixing with propeller mixer for 2 hours. The emulsion is then filtered through milipore filter with 8 μm pores and washed 5 times with 100 ml of distilled water.

Thereafter the procedure of Example 1 is followed to give TAP-144 microcapsules for injection.

What we claim is:

1. A prolonged release microcapsule having an average diameter of about 2 to 200μm for injection, which is produced by preparing a water-in-oil emulsion comprising an inner aqueous layer containing a biologically active polypeptide, a drug retaining substance therefor selected from a member of the group consisting of gelatin, albumin, pectin and agar and an oil layer containing a polymer substance of lactic acid-glycolic acid copolymer or lactic acid polymer, then thickening or solidifying said inner aqueous layer to a viscosity of not lower than about 5000 centipoises and finally admixing the resulting emulsion with a third aqueous layer to give a water/oil/water ternary layer emulsion and then desorbing the solvent in the oil layer.

2. A microcapsule as claimed in claim 1, wherein the biologically active polypeptide is (Pyr) Glu-His-Trp-Ser-Tyr-D-Leu-Leu-Arg-Pro-NH-$C_2H_5$.

3. A microcapsule as claimed in claim 1, wherein the drug retaining substance is gelatin.

4. A microcapsule as claimed in claim 1, wherein the polymer substance in the oil layer is a copolymer of lactic acid and glycolic acid.

5. A microcapsule as claimed in claim 4, wherein the ratio of lactic acid:glycolic acid is 75:25.

6. A microcapsule as claimed in claim 1, wherein the polymer substance in the oil layer is polylactic acid.

7. A microcapsule as claimed in claim 1, wherein the inner aqueous layer is thickened to a viscosity not less than about 10,000 centipoises.

8. A microcapsule as claimed in claim 1, wherein the inner aqueous layer is solidified.

9. A method for producing a prolonged release microcapsule having an average diameter of about 2 to 200 µm for injection, which comprises preparing a water-in-oil emulsion comprising an inner aqueous layer containing a biologically active polypeptide, a drug retaining substance therefor selected from a member of the group consisting of gelatin, albumin, pectin and agar and an oil layer containing a polymer substance of lactic acid-glycolic acid copolymer or lactic acid polymer, then thickening or solidifying said inner aqueous layer to a viscosity of not lower than about 5000 centipoises and finally admixing the resulting emulsion with a third aqueous layer to give a water/-oil/water ternary layer emulsion and then desorbing the solvent in the oil layer.

* * * * *